United States Patent
Bolner et al.

(10) Patent No.: US 10,463,476 B2
(45) Date of Patent: Nov. 5, 2019

(54) BODY NOISE REDUCTION IN AUDITORY PROSTHESES

(71) Applicant: Cochlear Limited, Macquarie University, NSW (AU)

(72) Inventors: Federico Bolner, Mechelen (BE); Adam Hersbach, East Melbourne (AU)

(73) Assignee: COCHLEAR LIMITED, Macquarie University, NSW (AU)

( * ) Notice: Subject to any disclaimer, the term of this patent is extended or adjusted under 35 U.S.C. 154(b) by 260 days.

(21) Appl. No.: 15/581,200

(22) Filed: Apr. 28, 2017

(65) Prior Publication Data

US 2018/0317027 A1    Nov. 1, 2018

(51) Int. Cl.
| | |
|---|---|
| A61F 2/18 | (2006.01) |
| H04R 25/00 | (2006.01) |
| A61N 1/36 | (2006.01) |
| H04R 3/00 | (2006.01) |

(52) U.S. Cl.
CPC ............ *A61F 2/18* (2013.01); *A61N 1/36036* (2017.08); *H04R 25/554* (2013.01); *H04R 3/005* (2013.01); *H04R 2225/67* (2013.01); *H04R 2410/05* (2013.01)

(58) Field of Classification Search
CPC ................ H04R 25/505; H04R 25/606; H04R 2225/67; H04R 2225/43; A61N 1/36036; A61F 2/18; A61F 2002/183
USPC ......................................................... 381/326
See application file for complete search history.

(56) References Cited

U.S. PATENT DOCUMENTS

| | | | |
|---|---|---|---|
| 6,707,920 B2 | 3/2004 | Miller | |
| 6,888,949 B1 | 5/2005 | Vanden Berghe et al. | |
| 7,853,031 B2 | 12/2010 | Hamacher | |
| 8,014,871 B2 | 9/2011 | Dalton et al. | |
| 8,096,937 B2 | 1/2012 | Miller, III | |
| 8,204,252 B1 * | 6/2012 | Avendano | H04R 3/005 |
| | | | 381/92 |
| 8,472,654 B2 | 6/2013 | Miller, III | |

(Continued)

FOREIGN PATENT DOCUMENTS

JP    2010-154432 A    7/2010

OTHER PUBLICATIONS

International Search Report and Written Opinion in corresponding International Application No. PCT/IB2018/052663, dated Aug. 3, 2018, 13 pages.

(Continued)

*Primary Examiner* — Oyesola C Ojo

(74) *Attorney, Agent, or Firm* — Edell, Shapiro & Finnan, LLC

(57) ABSTRACT

Presented herein are signal processing techniques that integrate an adaptive filtering process with a parametric post-filter in the frequency domain to control the amount of body noise reduction in each of a plurality of frequency bands (e.g., tuneable body noise reduction in each frequency band). The parametric post-filter generates a gain mask that is tuned to responses of sensors to separate external acoustic sounds and body noises, while limiting distortions of own voice. The techniques presented herein can preserve external acoustic sound quality, attenuate own voice to a comfortable level without distortion, suppress body noises, and/or lower a noise floor of the output signal.

27 Claims, 9 Drawing Sheets

(56) References Cited

U.S. PATENT DOCUMENTS

| | | | |
|---|---|---|---|
| 8,787,587 B1* | 7/2014 | Murgia | H04R 3/005 381/103 |
| 9,224,393 B2 | 12/2015 | Kjems et al. | |
| 2002/0138115 A1* | 9/2002 | Baumann | H04R 25/505 607/57 |
| 2003/0171787 A1 | 9/2003 | Money et al. | |
| 2005/0101831 A1 | 5/2005 | Miller et al. | |
| 2006/0155346 A1 | 7/2006 | Miller | |
| 2006/0183965 A1 | 8/2006 | Kasic et al. | |
| 2007/0009132 A1 | 1/2007 | Miller | |
| 2007/0021647 A1 | 1/2007 | Slattery et al. | |
| 2009/0187065 A1 | 7/2009 | Basinger | |
| 2009/0304215 A1* | 12/2009 | Hansen | G10L 21/0208 381/317 |
| 2010/0310084 A1* | 12/2010 | Hersbach | H04R 25/453 381/71.6 |
| 2010/0317913 A1 | 12/2010 | Conn et al. | |
| 2011/0098785 A1 | 4/2011 | Mishra | |
| 2011/0178438 A1 | 7/2011 | Van Gerwen | |
| 2011/0200222 A1 | 8/2011 | Miller, III et al. | |
| 2011/0319703 A1* | 12/2011 | Wiskerke | H04R 25/30 600/25 |
| 2012/0179462 A1* | 7/2012 | Klein | G10L 21/0208 704/226 |
| 2012/0232333 A1 | 9/2012 | Miller, III | |
| 2012/0239385 A1* | 9/2012 | Hersbach | G10L 25/84 704/200.1 |
| 2013/0079634 A1 | 3/2013 | Kerber | |
| 2013/0129115 A1* | 5/2013 | Smaragdis | H03G 3/002 381/107 |
| 2013/0156202 A1 | 6/2013 | Hamacher | |
| 2013/0281765 A1* | 10/2013 | Miller, III | A61B 5/721 600/25 |
| 2014/0012350 A1 | 1/2014 | Kasic, II et al. | |
| 2014/0073841 A1* | 3/2014 | Maier | H04R 1/222 600/25 |
| 2015/0112672 A1* | 4/2015 | Giacobello | H04M 9/082 704/233 |
| 2015/0201287 A1* | 7/2015 | Jespersgaard | H04R 25/50 381/321 |
| 2015/0256949 A1 | 9/2015 | Vanpoucke et al. | |
| 2015/0367132 A1 | 12/2015 | Milczynski et al. | |
| 2016/0119724 A1* | 4/2016 | Mauger | G10L 21/0264 607/57 |
| 2016/0165362 A1 | 6/2016 | Hubert-Brierre et al. | |
| 2017/0180876 A1* | 6/2017 | Theill | H04R 25/356 |

OTHER PUBLICATIONS

Kaibao Nie et al., "Encoding Frequency Modulation to Improve Cochlear Implant Performance in Noise", In: IEEE Transactions on Biomedical Engineering, Jan. 2005, vol. 52, Issue 1, pp. 64-73 ("http://ieeexplore.ieee.org/xpls/abs_all.jsp?arnumber=1369589").

Herman A. Jenkins et al., "Speech Perception Comparisons Using an Implanted and an External Microphone in Existing Cochlear Implant Users", Otology & Neurotology, Jan. 2012, vol. 33, No. 1, Department of Otolaryngology, University of Colorado School of Medicine, Aurora, Colorado, U.S.A.

* cited by examiner

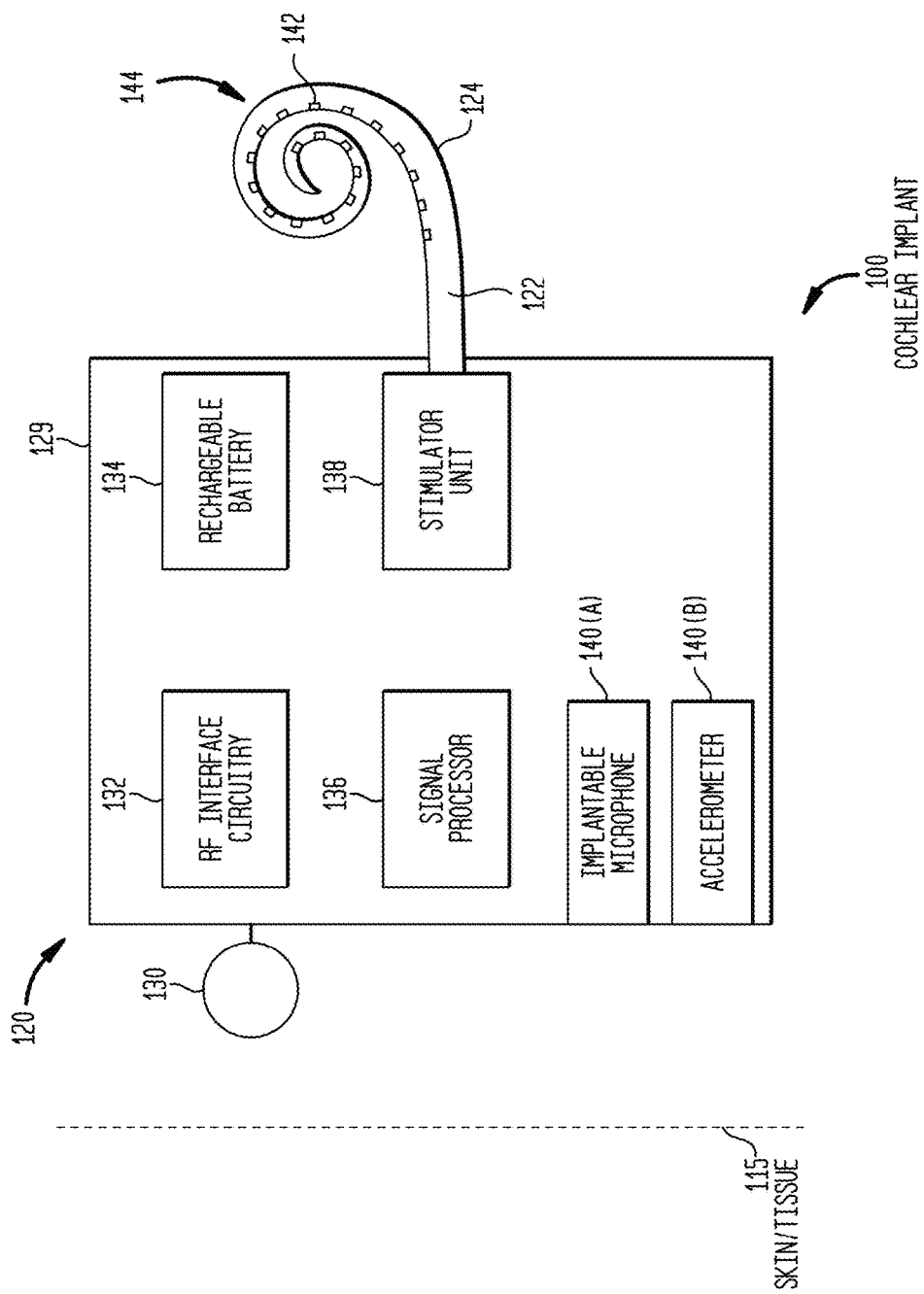

- 902 — DETECTING SIGNALS AT TWO OR MORE IMPLANTABLE SENSORS, WHEREIN THE SIGNALS DETECTED AT EACH OF THE TWO OR MORE IMPLANTABLE SENSORS COMPRISE ONE OR MORE OF EXTERNAL ACOUSTIC SOUNDS AND BODY NOISES

- 904 — GENERATING, FROM THE SIGNALS DETECTED AT THE TWO OR MORE IMPLANTABLE SENSORS, A SPEECH REFERENCE SIGNAL AND A NOISE REFERENCE SIGNAL

- 906 — GENERATING, WITH A PARAMETRIC POST-FILTER, A GAIN MASK BASED ON THE SPEECH REFERENCE SIGNAL AND THE NOISE REFERENCE SIGNAL

- 908 — GENERATING OUTPUT SIGNALS BASED ON THE SIGNALS DETECTED AT THE TWO OR MORE IMPLANTABLE SENSORS AND THE GAIN MASK, WHEREIN THE OUTPUT SIGNALS HAVE A SUBSTANTIALLY REDUCED AMOUNT OF BODY NOISE AND WHERE THE SHAPE OF THE POWER SPECTRUM OF ANY RESIDUAL BODY NOISE IS SUBSTANTIALLY MAINTAINED

US 10,463,476 B2

BODY NOISE REDUCTION IN AUDITORY PROSTHESES

BACKGROUND

Field of the Invention

The present invention relates generally to body noise reduction in auditory prostheses.

Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. An auditory brainstem stimulator is another type of stimulating auditory prosthesis that might also be proposed when a recipient experiences sensorineural hearing loss due to damage to the auditory nerve.

SUMMARY

In one aspect, a signal processing method is provided. The method comprises: detecting signals at two or more implantable sensors, wherein the signals comprise external acoustic sounds and body noises; generating, from the signals detected at the two or more implantable sensors, a speech reference signal and a noise reference signal; generating, with a parametric post-filter, a gain mask based on the speech reference signal and the noise reference signal; and generating output signals based on the signals detected at the two or more implantable sensors and the gain mask, wherein the output signals have a substantially reduced amount of body noise and where the amount of noise reduction is similar across frequencies thereof.

In another aspect, an auditory prosthesis is provided. The auditory prosthesis comprises: at least first and second implantable sensors configured to detect signals, wherein the second sensor is configured to be more sensitive to body noises than it is to external acoustic sound signals; and a signal processor configured to generate output signals from the signals, wherein the signal processor comprises: an input stage configured to generate a speech reference signal and a noise reference signal from the signals, a parametric post-filter configured to generate a gain mask based on the speech reference signal and the noise reference signal, and an output stage configured utilize the gain mask to generate the output signals, wherein the gain mask is configured to normalize a signal-to-noise ratio separately in each of the frequency channels in the output signals taking into account the differences in responses of the first and second implantable sensors during detection of body noise only and external acoustic sound only.

In another aspect, an auditory prosthesis is provided. The auditory prosthesis comprises: a multi-channel implantable sensor system configured to detect signals; a signal processor comprising an adaptive filtering block operable with a parametric post-filter in the frequency domain, wherein the adaptive filtering block and the parametric post-filter are collectively configured to convert the signals into output signals and to control the amount of body noise reduction in each of a plurality of frequency bands of the output signals; and an implantable stimulator unit configured to generate, based on the outputs signals, stimulation signals for delivery to a recipient of the auditory prosthesis to evoke perception by the recipient of the signals.

BRIEF DESCRIPTION OF THE DRAWINGS

Embodiments of the present invention are described herein in conjunction with the accompanying drawings, in which:

FIG. 1B is a block diagram of the cochlear implant of FIG. 1A;

FIG. 9 is a flowchart of a method, in accordance with certain embodiments presented herein.

DETAILED DESCRIPTION

Embodiments of the present invention are generally directed to signal processing techniques that integrate an adaptive filtering process with a parametric post-filter (parametric gain function) in the frequency domain, to separately control the amount of body noise reduction in each of a plurality of frequency bands (e.g., tuneable body noise reduction in each frequency band). The parametric post-filter generates a gain mask that is tuned to responses of sound and vibration sensors to separate external acoustic sounds and body noises, while limiting distortions induced by the noise reduction (especially affecting own voice). The techniques presented herein can preserve external acoustic sound quality, attenuate own voice to a comfortable level without distortion, suppress body noises, and/or lower the noise floor of the output signal. In certain embodiments presented herein, the techniques presented herein substantially maintain the shape of the power spectrum of any residual body noise (i.e., maintain the shape of any body noise remaining in the output). In certain embodiments, the amount of distortion of the residual body noise is controlled/regulated by the parametric post-filter/during the parametric post-filtering stage.

Merely for ease of illustration, the techniques presented herein are primarily described with reference to one type of auditory prosthesis, namely a cochlear implant. However, it is to be appreciated that the techniques presented herein may be used in other auditory prostheses, such as auditory brainstem stimulators, middle ear prosthesis, direct cochlear stimulators, electro-acoustic prostheses, etc.

Figure 1A:
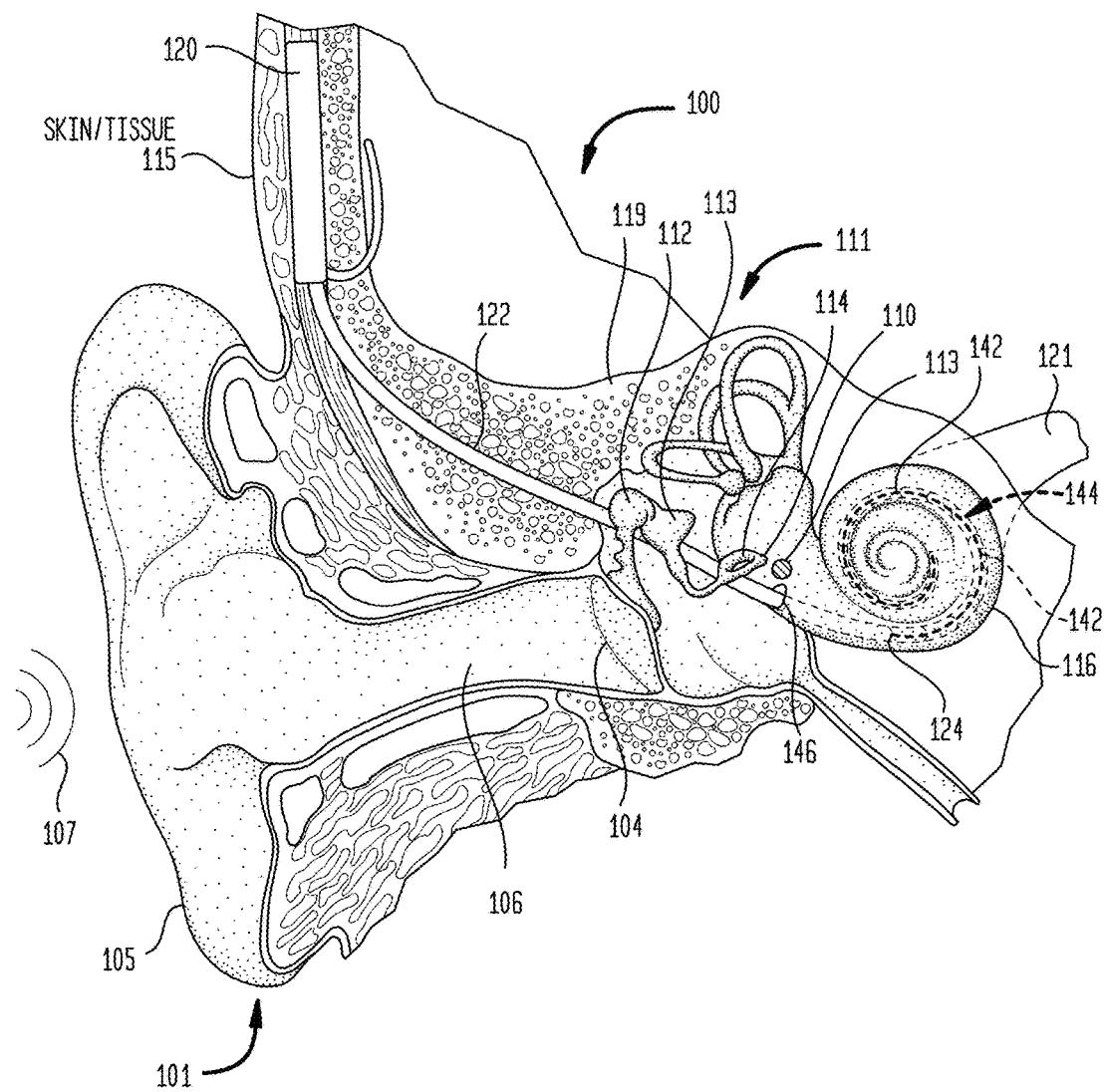
FIG. 1A is a schematic diagram illustrating a cochlear implant, in accordance with certain embodiments presented herein.

FIG. 1A is schematic diagram of an exemplary cochlear implant 100 configured to implement embodiments of the present invention, while FIG. 1B is a block diagram of the cochlear implant 100. For ease of description, FIGS. 1A and 1B will be described together.

Shown in FIG. 1A is an outer ear 101, a middle ear 102 and an inner ear 103 of the recipient. In a fully functional human hearing anatomy, the outer ear 101 comprises an auricle 105 and an ear canal 106. Sound signals 107, sometimes referred to herein as acoustic sounds or sound waves, are collected by the auricle 105 and channeled into and through the ear canal 106. Disposed across the distal end of the ear canal 106 is a tympanic membrane 104 which vibrates in response to the sound signals (i.e., sound waves) 107. This vibration is coupled to the oval window or fenestra ovalis 110 through three bones of the middle ear 102, collectively referred to as the ossicular chain or ossicles 111 and comprising the malleus 112, the incus 113 and the stapes 114. The ossicles 111 of the middle ear 102 serve to filter and amplify the sound signals 107, causing oval window 110 to vibrate. Such vibration sets up waves of fluid motion within the cochlea 116 which, in turn, activates hair cells (not shown) that line the inside of the cochlea 116. Activation of these hair cells causes appropriate nerve impulses to be transferred through the spiral ganglion cells and the auditory nerve 118 to the brain (not shown), where they are perceived as sound.

As noted above, sensorineural hearing loss may be due to the absence or destruction of the cochlea hair cells, which transduce acoustic signals into nerve impulses. One treatment for such hearing loss is a cochlear implant, such as cochlear implant 100 shown in FIGS. 1A and 1B, which bypasses the cochlear hair cells and delivers stimulation (e.g., electrical stimulation) directly to the cochlea nerve cells.

In the illustrative embodiment of FIGS. 1A and 1B, the cochlear implant 100 is a totally implantable cochlear implant, meaning that all components of the cochlear implant are configured to be implanted under skin/tissue 115 of a recipient. Because all components of cochlear implant 100 are implantable, the cochlear implant operates, for at least a finite period of time, without the need of an external device. An external device can be used to, for example, charge an internal power source (battery) of the cochlear implant 100.

The cochlear implant 100 comprises an implant body or main module 120, a lead region 122, and an elongate intra-cochlear stimulating assembly 124. The implant body 120 comprises a hermetically sealed housing 129 in which radio frequency (RF) interface circuitry 132 (sometimes referred to as a transceiver unit), at least one rechargeable battery 134, a signal processor 136, and a stimulator unit 138 are disposed. The implant body 120 also comprises a an internal/implantable coil 130, generally disposed outside of the housing 129, and at least two implantable sensors/transducers 140(A) and 140(B), which may located within the housing 129 or external to the housing 129. As such, although for ease of illustration the implantable sensors 140(A) and 140(B) are shown within housing 129, it is to be appreciated that the implantable sensors 140(A) and 140(B) may have other implanted positions/locations.

The RF interface circuitry 132 is connected to the implantable coil 130 and, generally, a magnet (not shown) is fixed relative to the implantable coil 130. Implantable coil 130 is typically a wire antenna coil comprised of multiple turns of electrically insulated single-strand or multi-strand platinum or gold wire. The electrical insulation of implantable coil 130 is provided by a flexible molding (e.g., silicone molding), which has been omitted from FIG. 1B. In general, the implantable coil 130 and the RF interface circuitry 132 enable the transfer of power and/or data from an external device to the cochlear implant 100. However, it is to be appreciated that various types of energy transfer, such as infrared (IR), electromagnetic, capacitive and inductive transfer, may be used to transfer power and/or data from an external device to a cochlear implant 100 and, as such, FIG. 1B illustrates only one example arrangement.

Elongate stimulating assembly 124 is configured to be at least partially implanted in cochlea 116 and includes a plurality of longitudinally spaced intra-cochlear electrical stimulating contacts (electrical contacts) 142 that collectively form a contact array 144. Stimulating assembly 124 extends through an opening in the cochlea 116 (e.g., cochleostomy 146, oval window 110, the round window 113, etc.) and has a proximal end connected to stimulator unit 138 via lead region 122 that extends through mastoid bone 119. Lead region 122 couples the stimulating assembly 124 to implant body 120 and, more particularly, to stimulator unit 138.

As noted above, the cochlear implant 100 comprises at least two implantable sensors 140(A) and 140(B), where one sensor is more sensitive to body noises than it is to external acoustic sound signals. In the illustrative embodiment of FIG. 1B, the implantable sensor 140(A) is a "sound" sensor/transducer that is primarily configured to detect/receive external acoustic sounds (e.g., an implantable microphone), while the implantable sensor 140(B) is a "vibration" sensor that is primarily configured to detect/receive internal body noises (e.g., another implantable microphone or an accelerometer). For ease of description, embodiments presented herein will be primarily described with reference to the use of an implantable microphone 140(A) as the sound sensor and an accelerometer 140(B) as the vibration sensor. However, it is to be appreciated that these specific implementations are non-limiting and that embodiments of the present invention may be used with different types of implantable sensors.

As noted, the implantable microphone 140(A) and the accelerometer 140(B) may each be disposed in, or electrically connected to, the implant body 120. In operation, the microphone 140(A) and the accelerometer 140(B) detect input (sound/vibration) signals (e.g., external acoustic sounds and/or body noises) and convert the detected input signals into electrical signals. These electrical signals are received by the signal processor 136, which is configured to execute signal processing and coding to convert the electrical signals into processed signals that represent the detected signals. The processed signals are then provided to the stimulator unit 138, which is configured to utilize the processed signals to generate electrical stimulation signals that are delivered to the recipient's cochlea via one or more electrodes 142 implanted in the recipient's cochlea 116. In this way, cochlear implant 100 stimulates the recipient's auditory nerve cells, bypassing absent or defective hair cells that normally transduce acoustic vibrations into neural activity.

It is generally desirable for implantable cochlear implants, such as cochlear implant 100, to be capable of achieving sufficient signal-to-noise ratio (SNR), while being sufficiently insensitive to biological/body noises. As used herein, body noises (BNs) are undesirable sounds induced by the body that are propagated primarily as vibration, such as breathing, scratching, rubbing, noises associated with the movement of the head, chewing, etc. Own voice (OV) (i.e., when the recipient speaks) is a particular case of body noise since the sound is transmitted both through air conduction and bone conduction (i.e., skull vibrations). In certain own voice instances, most of these sound propagates through the skull bones and produce accelerations at the implantable microphone. These vibrations need to be controlled in order to deliver a useful signal to the recipient. That is, in general, subcutaneous/implantable microphones are affected by body noises that can be characterized as an acceleration coming from the body (or the recipient's own voice), and captured by the microphone. In the case of own voice, the bone conducted vibrations are loud and, in conventional arrangements, cannot be easily differentiated from other body noises, thus degrading the perception of the recipient's own voice when conventional body noise reduction is performed. As such, there is a need to attenuate own voice and other body noise levels without causing distortion, as perception of own voice is important to speaking well, and long term to exposure to poor own voice perception can negatively affect the way recipients speak.

Various microphone structures which reduce detected body noises have been proposed. For example, multi-channel implantable sensor systems/arrays, which include two or more implanted sensors/transducers placed inside the body of the recipient (e.g., under his/her skin) have been proposed. However, these multi-channel implantable sensor systems may still be significantly affected by body noises. In addition, conventional signal processing techniques are limited in the amount of body noise reduction that can be achieved due to the fact that these techniques inherently introduce distortion into the output. As such, conventional signal processing techniques may try to achieve a balance or tradeoff between the amount body noise reduction and the amount of distortions that are introduced. The signal processing techniques in accordance with the embodiments of the present invention reduce or substantially eliminate the need for such tradeoffs and can achieve the same noise reduction with less distortions and/or can improve noise reduction with the same amount of distortions. As described further below, this is achieved in the signal processing techniques presented herein by integrating an adaptive filtering process with a parametric post-filter (parametric gain function) in the frequency domain, to separately control the amount of body noise reduction in each of a plurality of frequency bands (e.g., tuneable body noise reduction in each frequency band). The parametric post-filter generates a gain mask that is tuned to separate external speech and body noises, while limiting distortions of own voice. The techniques presented herein can preserve external acoustic sound quality, attenuate own voice to a comfortable level without distortion, suppress body noises, and/or lower a noise floor of the output signal.

The signal processing techniques presented herein leverage the use of multi-channel implantable sensor systems to provide the ability to achieve the same amount of noise reduction with less distortions and/or can improve noise reduction with the same amount of distortions. In particular, as described further below, the techniques presented herein are configured to generate output signals based on the signals detected at the two or more implantable sensors, wherein the output signals have a substantially reduced amount of body noise and where the shape of the power spectrum of any residual/remaining body noise is substantially maintained. The techniques presented herein are generally described with reference to multi-channel implantable sensor systems where at least one of the sensors is designed to be more sensitive to bone-transmitted vibrations than it is to acoustic (air-borne) sound waves. These sensors can take a variety of different forms, such as microphones, accelerometers, etc. For ease of illustration, the techniques presented herein are described with reference to a dual-channel implantable system where the sensor that is more sensitive to bone-transmitted vibrations is referred to as an "accelerometer" (e.g., accelerometer 140(B) of FIG. 1B) and the other sensor is referred to as a microphone (e.g., microphone 140(A) of FIG. 1B). The increased sensitivity of the accelerometer 140(B) to body noise may be due to, for example, the structure of the accelerometer 140(B) relative to the microphone 140(A), the implanted position of the accelerometer 140(B) relative to the microphone 140(A), etc. For example, in certain embodiments, the accelerometer 140(B) and the microphone 140(A) are structurally similar but they are placed in different locations which accounts for the body noise sensitivity difference.

Figure 2:
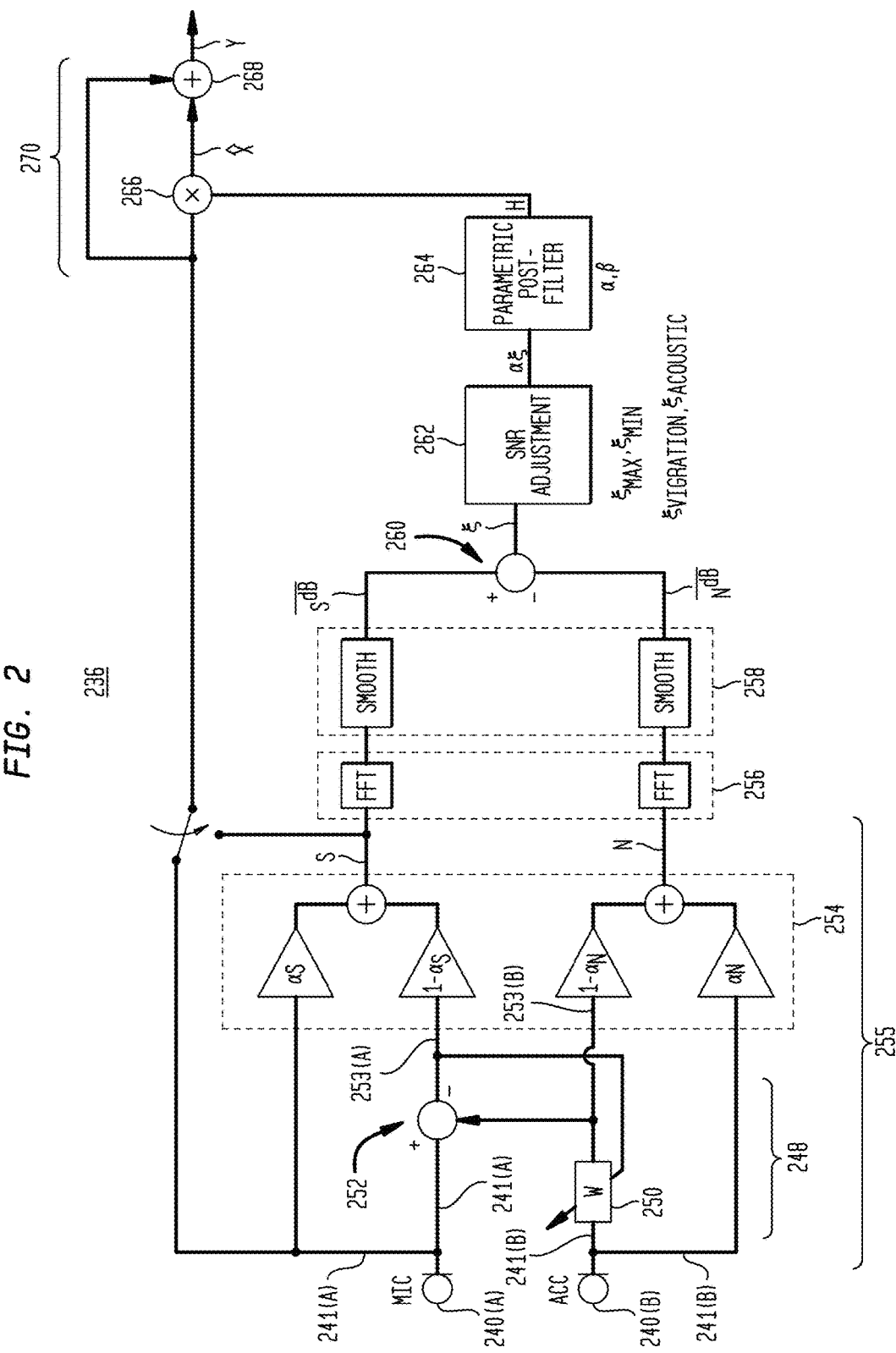
FIG. 2 is a schematic diagram illustrating operations of a signal processor, in accordance with certain embodiments presented herein.

FIG. 2 is a schematic block diagram illustrating operations of a portion of an auditory prosthesis signal processor 236 that is configured to execute the signal processing techniques presented herein. As described further below, the signal processor 236 is configured to reduce body noises, while at the same time limiting the introduction of distortions. Shown in the illustrative embodiment of FIG. 2 is a microphone 240(A) and an accelerometer 240(B) that are configured to detect signals, including external acoustic sounds and/or body noises. The accelerometer 240(B) is configured to be more sensitive to bone-transmitted vibrations (i.e. body noise) than is the microphone 240(A). This increased sensitivity of the accelerometer 240(B) to body noise may be due to, for example, the structure of the accelerometer 240(B) relative to the microphone 240(A), the implanted position of the accelerometer 240(B) relative to the microphone 240(A), etc. For example, in certain embodiments, the accelerometer 240(B) and the microphone 240(A) are structurally similar but they are placed in different locations which accounts for the body noise sensitivity difference. FIG. 2 also illustrates an adaptive filtering stage 248, which comprises an adaptive filter 250 and a noise canceller 252, a regulation block/stage 254, a frequency domain conversion block 256, a smoothing block 258, a signal-to-noise ratio (SNR) estimator 260, an SNR adjustment block 262, a parametric post-filter 264, a gain mask application module 266, and an output block 268. It is to be appreciated that the various elements shown in FIG. 2 may, in certain examples, be controlled by one or more control units which, for ease of illustration, have been omitted from FIG. 2.

In accordance with certain embodiments presented herein, the adaptive filtering block 248 and the regulation block 254 are sometimes collectively referred to herein as an "input stage" 255 of the signal processor 236. In addition, the gain mask application module 266 and the output block 268 are sometimes collectively referred to herein as an "output stage" 270 of the signal processor 236.

In operation, input signals (i.e., external acoustic sounds and/or body noises) are detected at/by the microphone 240(A) and the accelerometer 240(B), which convert the detected input signals (sound/vibration signals) into electrical signals. The electrical signals output by the microphone 240(A) are referred to herein as the "unprocessed microphone signals" 241(A) (microphone signals), while the output of electrical signals output by the accelerometer 240(B) are referred to herein as the "unprocessed accelerometer signals" 241(B) (accelerometer signals). The microphone signals 241(A) and the accelerometer signals 241(B) are used by the adaptive filtering block 248 (i.e., by the adaptive filter 250 and the noise canceller 252) to generate a speech estimate 253(A) and a noise estimate 253(B), which are provided to the regulation block 254. That is, the adaptive filtering block 248 generates a speech estimate 253(A) and a noise estimate 253(B) from the microphone and accelerometer signals. The adaptive filter 250 may comprise, for example, a Normalized Least Mean Square (NLMS) adaptive filter, a Frequency-domain adaptive filter (FDAF), a Weiner filter, etc.

Also shown in FIG. 2 is the regulation block 254 is configured to use the speech estimate 253(A) and the noise estimate 253(B) to generate a "speech reference signal" (S), and a "noise reference signal" (N). In general, the speech reference signal includes an estimate of useful acoustically-transmitted soundwaves (i.e., external acoustic sounds) and the noise reference signal includes an estimate of the bone-transmitted body noise vibrations (i.e., body noises).

In the regulation block 254, two parameters referred to as smoothing constants "$\alpha_S$" and "$\alpha_N$" regulate the proportion of the raw, unprocessed microphone signals 241(A) and unprocessed accelerometer signals 241(B) that are mixed with the speech estimate 253(A) and the noise estimate 253(B), respectively, to generate the speech reference signal and the noise reference signal. That is, the value of $\alpha_S$ controls the amount of mixing of the unprocessed microphone signals 241(A) with the speech estimate 253(A), while the value of $\alpha_N$ controls the amount of mixing of the unprocessed accelerometer signals 241(B) with the noise estimate 253(B). The values of $\alpha_S$ and $\alpha_N$ may limit the how the adaptive filtering ultimately affects the speech reference signal and the noise reference signal.

The parameters $\alpha_S$ and $\alpha_N$ each have a numerical value between 0 and 1 (i.e., $0 \leq \alpha_S \leq 1$, $0 \leq \alpha_N \leq 1$) and when $\alpha_S$ and $\alpha_N$ each have a value of zero (i.e., $\alpha_S = \alpha_N = 0$), the speech reference signal and the noise reference signal are equivalent to the speech and noise estimates, respectively, generated by the adaptive filtering block 248. When $\alpha_S$ and $\alpha_N$ each have a value of one (i.e., $\alpha_S = \alpha_N = 1$), the speech reference signal and the noise reference signal are equivalent to the unprocessed microphone signals 241(A) and accelerometer signals 241(B), respectively.

As described further below, in accordance with embodiments of the present invention, the speech reference signal and the noise reference signal are used to calculate a parametric gain mask ($H_k[n]$) at each time index n which defines a gain ($H_k$) (i.e., the amount of noise reduction) to be applied in each of a plurality of frequency channels (k) associated with the signals. That is, the signals are split into plurality of components each within one of a plurality of frequency channels (k), and a gain is calculated for each of the frequency components. However, before calculation of parametric gain mask ($H_k[n]$) one or more intermediate operations are first performed using the speech reference signal and the noise reference signal. In certain arrangements, the speech reference signal and the noise reference signal are used to generate instantaneous signal-to-noise ratio (SNR) estimates for the plurality of frequency channels and the instantaneous SNR estimates are adjusted (e.g., normalized) to account for the difference between the responses of the sensors 240(A) and 240(B) to external acoustic sounds or body noises.

Depending on whether the adaptive filter block 248 operates in the time or frequency domain, before calculation of parametric gain mask ($H_k[n]$), a frequency domain conversion may be applied to the speech reference signal and the noise reference signal. FIG. 2 illustrates an example embodiment in which the speech reference signal and the noise reference signal are time domain signals, and a frequency domain conversion block 256 executes one or more Fast Fourier transforms (FFTs) to convert these time domain signals into frequency domain signals with multiple frequency channels k. At the output of the frequency domain conversion block 256, the speech reference signal is referred to as a frequency-domain speech reference, represented as $S^{dB}_k[n]$, and the noise reference signal is referred to as a frequency-domain noise reference, represented as $N^{dB}_k[n]$, where k is the frequency index and n is the time index of overlapping FFT windows. The speech and noise reference signals are preferably converted in the log-domain (dB) because it relates more closely to perceptual loudness.

FIG. 2 also illustrates the use of a smoothing block 258 (e.g., one or more smoothing filters) to reduce artifacts in the frequency-domain speech reference ($S^{dB}_k[n]$) and the frequency-domain speech reference ($N^{dB}_k[n]$). In the example of FIG. 2, the speech and noise references are transformed into the frequency domain and filtered separately using first-order Infinite Impulse Response (IIR) filters with independent attack and release times. The attack time ($\beta_A$) and the release time ($\beta_R$) each have a numerical value between zero and 1 (i.e., $0 \leq \beta_A \leq 1$, $0 \leq \beta_R \leq 1$). At the output of the smoothing block 258, the speech reference signal is sometimes referred to as a frequency-domain smoothed speech reference or, more simply, as a smoothed speech reference signal, while the noise reference signal is sometimes referred to as a frequency-domain smoothed noise reference signal or, more simply, as a smoothed noise reference signal. The smoothed speech reference signal is represented as $\overline{S^{dB}}_k[n]$, and the smoothed noise reference signal is represented as $\overline{N^{dB}}_k[n]$. The smoothed speech reference signal is given as shown below in Equation 1, while the smoothed noise reference signal is given as shown below in Equation 2.

$$\overline{S_k^{dB}}[n] = \beta_S S_k^{dB}[n] + (1-\beta_S)\overline{S_k^{dB}}[n-1], \quad \text{Equation 1}$$

$$\text{Where } \beta_S = \begin{cases} \beta_A, & S_k^{dB}[n] > \overline{S_k^{dB}}[n-1] \\ \beta_R, & \text{otherwise} \end{cases}$$

-continued $$\overline{N_k^{dB}}[n] = \beta_N N_k^{dB}[n] + (1-\beta_N)\overline{N_k^{dB}}[n-1], \quad \text{Equation 2}$$

$$\text{Where } \beta_N = \begin{cases} \beta_A, & \overline{N_k^{dB}}[n] > \overline{N_k^{dB}}[n-1] \\ \beta_R, & \text{otherwise} \end{cases}$$

Figure 3:
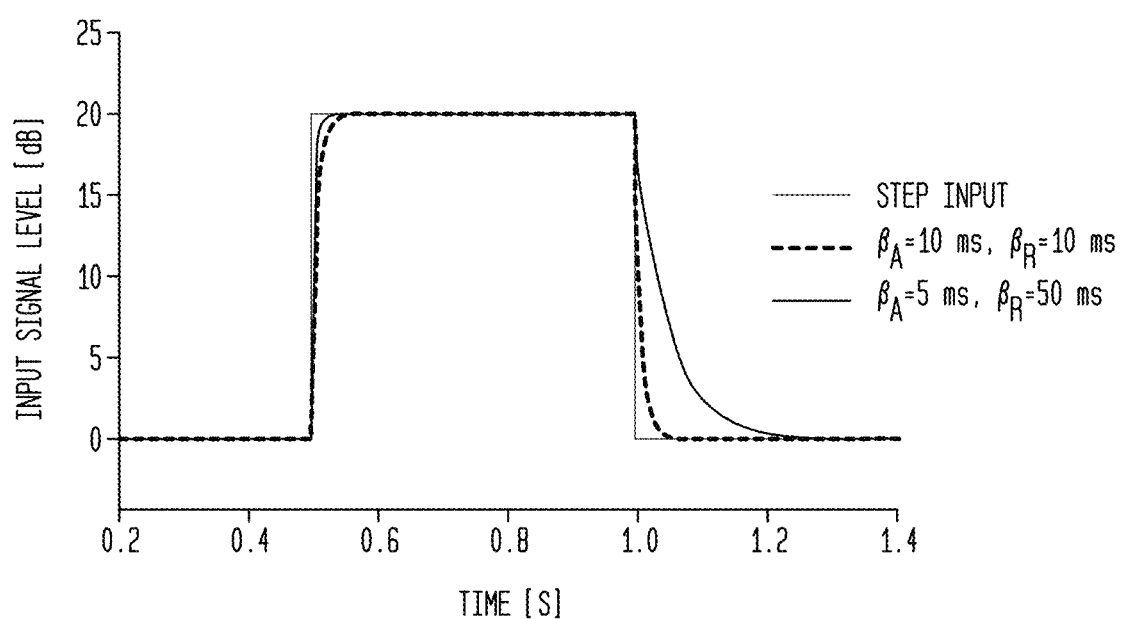
FIG. 3 is a graph illustrating the effect of a signal smoothing parameter for a step input change in input signal level, in accordance with certain embodiments presented herein.

FIG. 3 is a graph illustrating the effect of the signal smoothing parameter, β, for a step input change in input signal level showing symmetric and asymmetric attack and release time constants.

Returning to the embodiment of FIG. 2, the smoothed speech reference signal and the smoothed noise reference signal are used at the SNR estimator 260 to estimate the instantaneous SNR, given as $\xi_k[n]$ at each time point n and in each frequency band k. More specifically, the instantaneous SNR ($\xi_k[n]$) is given below in Equation 3 as, at each frequency, the difference between the smoothed speech reference signal and the smoothed noise reference signal at a given time point.

$$\xi_k[n] = \overline{S^{dB}}_k[n] - \overline{N^{dB}}_k[n] \quad \text{Equation 3:}$$

In accordance with embodiments presented herein, the instantaneous SNR estimate in each frequency band is adjusted/normalized in order to account for the difference between the sensor/transducer responses to external acoustic sounds and body noises (i.e., the differences in responses of the microphone 240(A) and accelerometer 240(B) to external acoustic sounds and body noises). The instantaneous SNR adjustment (normalization) operations are applied at the SNR adjustment block 262 and these operations are given as shown below in Equation 4.

$$a\xi_k[n] = \xi_k^{min} + \frac{\xi_k[n] - \xi_k^{vibration}}{\xi_k^{acoustic} - \xi_k^{vibration}}(\xi_k^{max} - \xi_k^{min}) \quad \text{Equation 4}$$

Where:
- $\xi_k[n]$ is the instantaneous SNR (in dB) at each time point n and in each frequency band k;
- $\xi^{max}$ and $\xi^{min}$ are the maximum and minimum SNRs, respectively, (in dB, broadband) to which the instantaneous SNR is to be remapped, which, in turn, define the minimum and maximum gain of the subsequent parametric Wiener gain mask;
- $\xi_k^{acoustic}$ is the average SNR measured during acoustic input (no body noise present) in each frequency band; and
- $\xi_k^{vibration}$ is the average SNR measured during body noise input (no acoustic input present) in each frequency band.

In certain embodiments, the values for $\xi_k^{acoustic}$, $\xi_k^{vibration}$, $\xi^{max}$, and $\xi^{min}$ are all pre-determined/pre-programmed values during, for example, a clinical fitting session in which the auditory prosthesis is "fit" or "customized" for the specific recipient. Since one objective of the techniques presented herein is control own voice distortions, the $\xi_k^{vibration}$ may be set to the SNR ($\xi_k$) during own voice. In certain embodiments, the $\xi_k^{acoustic_c}$ and the $\xi_k^{vibration}$ may be measured for each recipient, since each recipient will experience varying differences in the response of implanted sensors during acoustic and body noise (vibration) inputs depending on various recipient-specific parameters, such as microphone location, skin thickness, etc. In certain embodiments, $\xi^{max}$ and $\xi^{min}$ can be standardized and correlated to how much noise reduction is desired. For example, the $\xi^{max}$ and $\xi^{min}$ can be set to +20 dB and −20 dB, respectively, +10 dB and −10 dB, respectively, or other values.

As noted, the SNR adjustment at SNR adjustment block 262 is configured to normalize the SNR with the knowledge of what the SNR is during detection of acoustic sound signals only and what the SNR is during detection of body noises only, such as during detection of own voice (i.e., the SNR adjustment/normalization stage is designed to account for differences in the transducers, in their relative acoustic and vibration sensitivities). Equation 4 normalizes the SNR of the input signals detected by the microphone 240(A) and the accelerometer 240(B) between the $\xi^{max}$ and $\xi^{min}$, which are fixed parameters, while taking into account the SNR of the acoustic input and the SNR of body noise. The output of the SNR adjustment block 262 are adjusted SNR estimates for each of the k frequency bands. That is, the outcome of SNR adjustment bloc 262 is that, for a given input SNR, the noise reduction gain that is calculated is similar across frequency. The transducer dependent variation across frequency is thus removed (or reduced) by the SNR-normalization stage.

Figure 4:
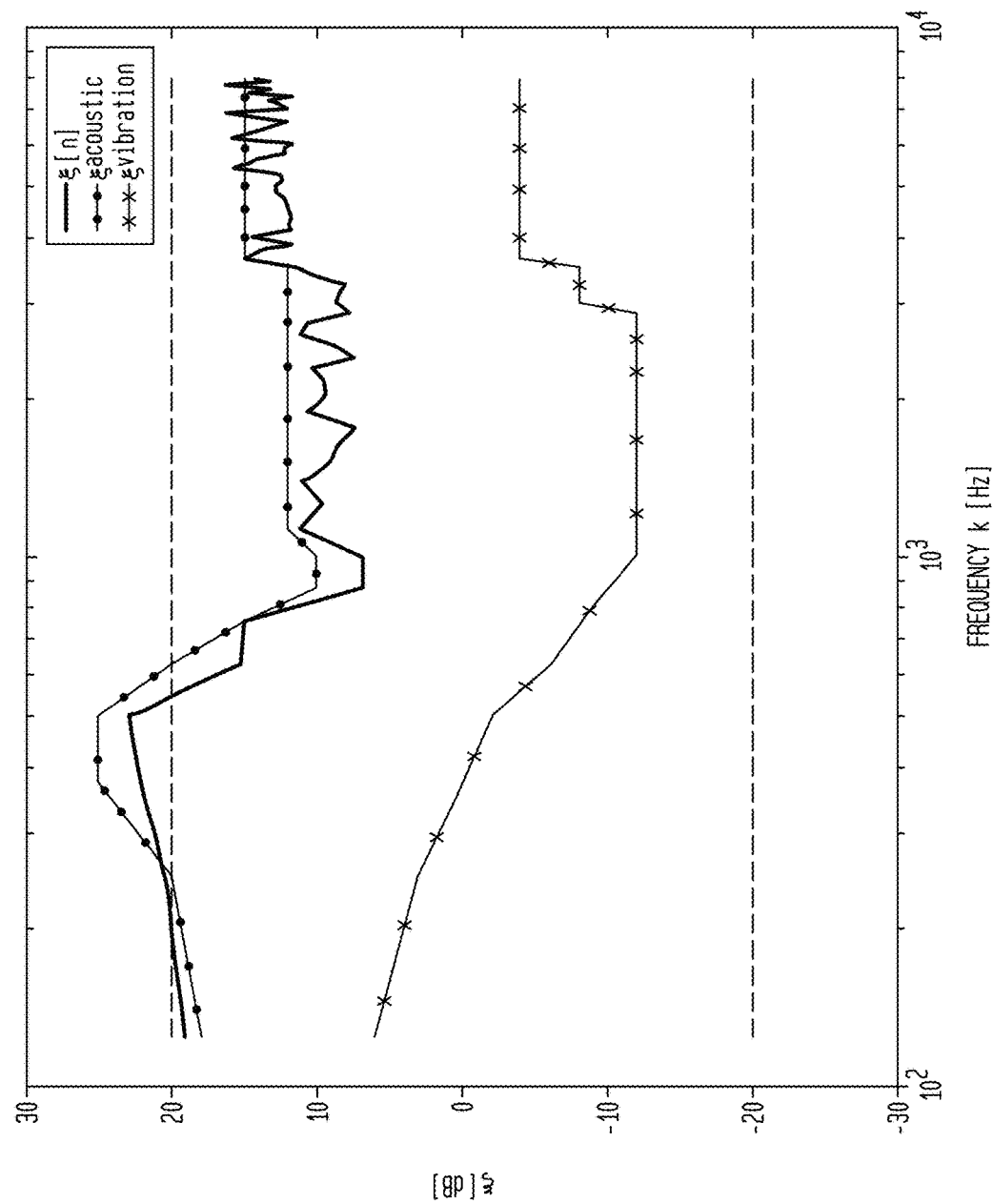
FIG. 4 is a graph illustrating example signal-to-noise ratio (SNR) adjustment parameters, in accordance with certain embodiments presented herein.

FIG. 4 is a graph illustrating example SNR adjustment parameters, where $\xi^{max}$ is set to 20 dB and $\xi^{min}$ is set to −20 dB (i.e., $\xi^{max}$ 20 dB and $\xi^{min}$=20 dB). In this example, when the instantaneous SNR corresponds to the $\xi_k^{acoustic}$, it will be mapped to $\xi^{max}$=+20 dB. When the instantaneous SNR corresponds to the $\xi_k^{vibration}$, it will be mapped to $\xi^{min}$=−20 dB. The same SNR across frequencies directly translates into the same gain when computing the gain mask and thus the same amount of attenuation.

Returning to the specific embodiment of FIG. 2, in certain instances, the calculated instantaneous SNR may be inaccurate. For frequency bands were the instantaneous SNR is inaccurate, for example in higher frequency bands (e.g., k2+1, . . . k3, etc.), the computed adjusted SNR can be replaced with a more appropriate value, such as the mean of the adjusted SNR in lower frequency bands [e.g., k1, . . . k2]. This replacement is represented below in Equation 5.

$$a\xi_{k2+1 \ldots k3} = E[a\xi_{k1 \ldots k2}] = \frac{1}{k2-k1+1}\sum_{k=k1}^{k=k2} a\xi_k, \quad \text{Equation 5}$$

$$0 < k1 < k2 < k3$$

Although Equation 5 illustrates the use of replacements at higher frequencies, it is to be appreciated that this specific replacement is illustrative. In other embodiments, replacement may not be needed to may be performed at different frequencies.

Returning to the specific embodiment of FIG. 2, as shown, the SNR adjustment is performed prior to the post-filtering process (i.e., prior to generation of a gain mask at the parametric post-filter 264). In general, and as noted above, the SNR is adjusted in a manner that normalizes the SNR separately in frequency band taking into account the differences in the sensor responses during detection of body noise only and external acoustic sound only (i.e., equalize the SNR according to the differences in the sensor responses in order to compensate for those differences). This results in output signals having approximately the same amount of (adjustable) body noise reduction across frequencies and thus helps to avoid distortions and, in particular, reduces own voice distortions. In addition, the output signals have a substantially reduced amount of body noise and where the shape of the power spectrum of any residual/remaining body noise is substantially maintained. As used herein, the "power spectrum" (also known as the "power spectral density") of the residual body noise (i.e., body noise remaining after post-filtering) describes the distribution of power into frequency components composing the signal. Substantially maintaining the shape of the power spectrum means that the residual body noise is substantially non-distorted. In certain embodiments, the amount of distortion of the residual body noise is controlled/regulated by the parametric post-filter/during the parametric post-filtering process.

The adjusted SNR estimate $\alpha\xi_k[n]$ is used as the primary mechanism to attenuate time-frequency bins that are considered noisy. More specifically, the adjusted SNR estimate ($\alpha\xi_k[n]$) is used as an input to the parametric post-filter 264, which is configured to generate a post-filter gain mask (i.e., gains at each of the k frequencies). In one specific embodiment, the parametric post-filter 264 is a parametric Wiener gain filter that generates a post-filter gain mask ($H_k[n]$), using adjustable bias ($\alpha$) and exponent ($\beta$) parameters, where the bias parameter is greater than zero (i.e., $\alpha$>0) and the exponent parameter is greater than zero (i.e., $\beta$>0). This is given below in Equation 6.

$$H_k[n] = \left(\frac{a\xi_k[n]}{\alpha + a\xi_k[n]}\right)^\beta \quad \text{Equation 6}$$

As noted above, FIG. 2 illustrates the presence of an SNR adjustment stage prior to the computation of the post-filter gain mask ($H_k[n]$). As such, the parameters $\alpha$ and $\beta$ in Equation 6 are frequency-independent (i.e., constant across the different frequencies k). In certain illustrative embodiments, $\alpha$=1 and $\beta$=0.5, but other values are possible. For example, in some further embodiments, $\alpha$ and $\beta$ can each be tuned to control the amount of noise reduction in different listening environments. For example, in listening conditions in which the SNR is high (e.g., when the SNR is above a predetermined threshold), $\alpha$ and $\beta$ can be tuned such that the noise reduction is less aggressive (e.g., $\alpha$=1 and $\beta$=0.5). Alternatively, in listening conditions in which the SNR is low (e.g., when the SNR is below a predetermined threshold), $\alpha$ and $\beta$ can be tuned such that the noise reduction is more aggressive (e.g., $\alpha$=3 and $\beta$=1).

It is to be noted that, in certain embodiments, the energy of the noise reference can be used in the same manner as well. This can be useful in case of loud vibrations caused by loud body noise, such as biting, scratching, etc. In these examples, the gain parameters could become increasingly aggressive (e.g. increasing $\beta$) as the energy of the noise reference increases.

As shown in FIG. 2, a clean signal $\hat{X}_k[n]$ is generated/estimated by applying the post-filter gain mask ($H_k[n]$) to a signal $S_k[n]$. In the example of FIG. 2, the post-filter gain mask ($H_k[n]$) is applied at the gain mask application module 266 and this application is given below in Equation 7.

$$\hat{X}_k[n] = H_k[n]S_k[n] \quad \text{Equation 7:}$$

Where $S_k[n]$ can either be:
(a) the unprocessed microphone signal 241(A), or
(b) the speech reference signal (S).

Figure 5A:
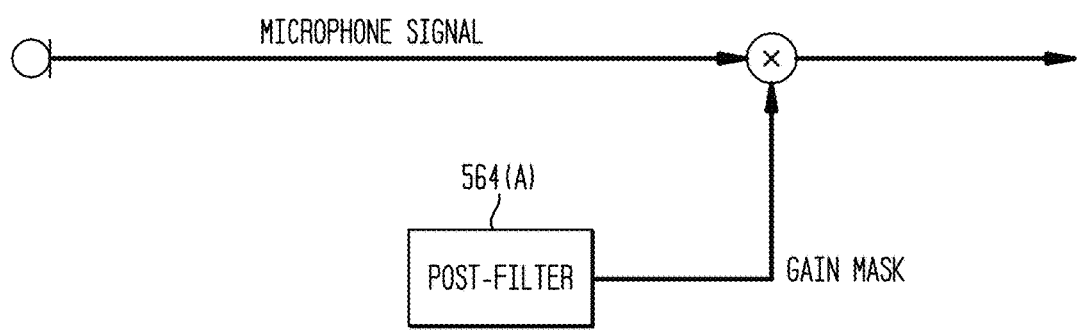
FIG. 5A is a schematic diagram illustrating application of a post-filter gain mask to a microphone signal, in accordance with certain embodiments presented herein.
Figure 5B:
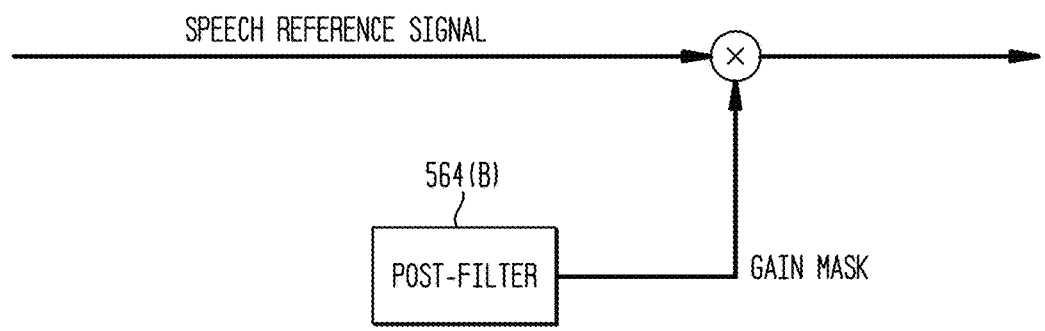
FIG. 5B is a schematic diagram illustrating application of a post-filter gain mask to a speech reference signal, in accordance with certain embodiments presented herein.

FIG. 5A is a schematic diagram illustrating application of a post-filter gain mask to an unprocessed microphone signal, while FIG. 5B is a schematic diagram illustrating application of a post-filter gain mask to a speech reference signal. More specifically, in the example of FIG. 5A, a post-filter gain mask generated by a post-filter 564(A) is applied to the noisy unprocessed microphone signal, which includes both the external acoustic sound and body noise (vibrations). In this case, the body noise reduction is performed by the gain application. In the example of FIG. 5B, a post-filter gain mask generated by a post-filter 564(B) is applied to the speech reference signal, which generally includes only residual body noises. In this case, the gains will equalize (i.e., even out) the attenuation of body noises across frequencies, attenuating the residual noise only.

In certain embodiments of FIGS. 5A and 5B, the post-filter 564(A) and/or the post-filter 564(B) may be similar to parametric post-filter 264 of FIG. 2 which uses an adjusted instantaneous SNR and frequency-independent parameters (e.g., frequency independent a and values, in the case of a parametric wiener filter). In alternative embodiments, the post-filter 564(A) and/or the post-filter 564(B) may be similar to post-filter 864 of FIG. 8 described further below which uses frequency-dependent parameters to perform a gain adjustment in the post-filter itself that mimics the above described SNR adjustment.

Again returning to the embodiment of FIG. 2, in certain instances output signals, represented as $Y_k[n]$, is formed at output block 268 from a weighted combination of the signal $S_k[n]$ (e.g., either the microphone signal or the speech reference signal) and the estimated clean signal ($\hat{X}_k[n]$) using a maximum attenuation parameter $\gamma$ to mix the two signals together. The maximum attenuation parameter $\gamma$ allows the output signals ($Y_k[n]$) to completely disable ($\gamma$=0) or completely enable ($\gamma$=1) the noise reduction processing, with a continuous and smooth transition between the two. This is given below in Equation 8.

$$Y_k[n] = \gamma\hat{X}_k[n] + (1-\gamma)S_k[n] \quad \text{Equation 8:}$$

Figure 6:
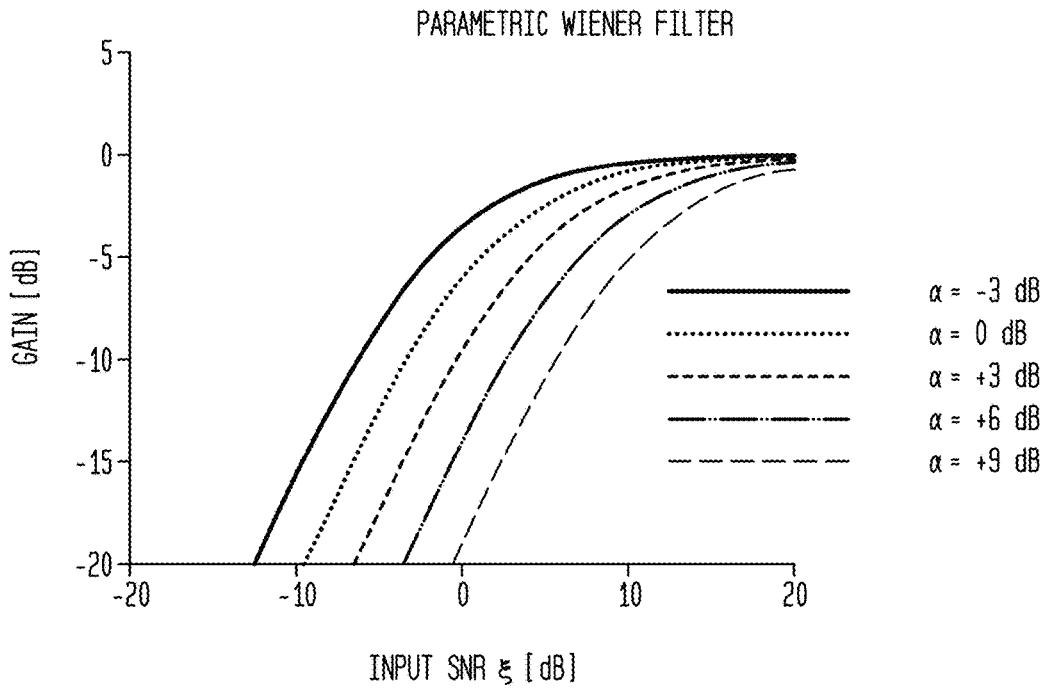
FIG. 6 is a graph illustrating the effect of a bias parameter of a parametric post-filter, for a range of values, in accordance with certain embodiments presented herein.
Figure 7:
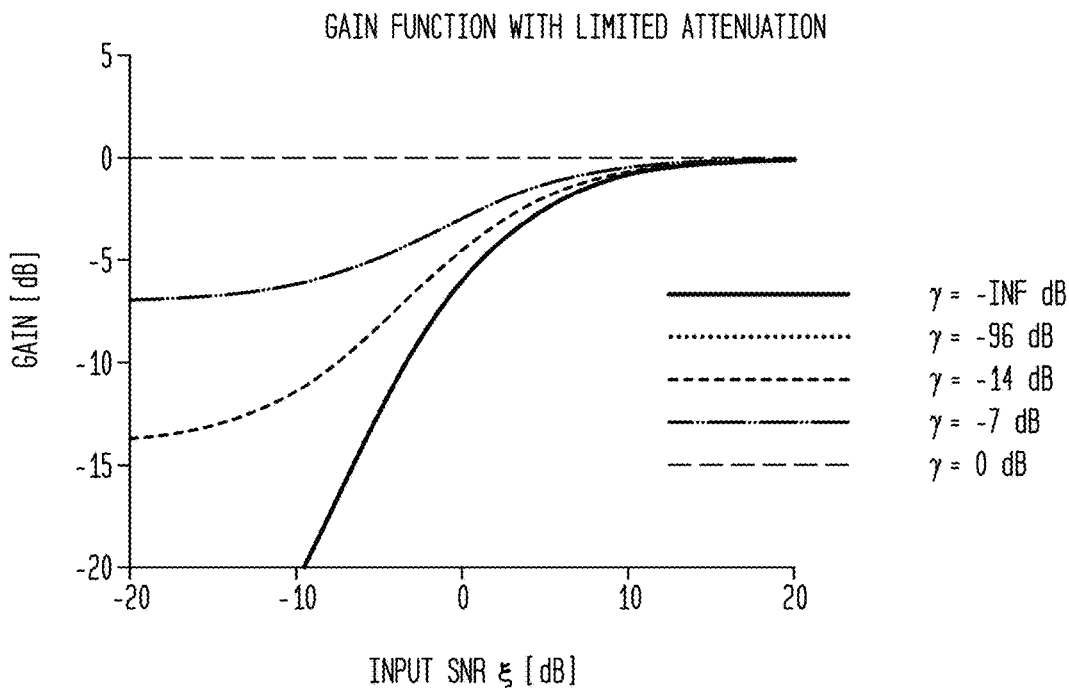
FIG. 7 is a graph illustrating the effect of a maximum attenuation parameter on gain values, in accordance with certain embodiments presented herein.

As noted above, certain embodiments presented herein may use a parametric wiener filter (which maps an input SNR to a gain value) in order to generate a gain mask for application to the signal $S_k[n]$ (e.g., either the microphone signal or the speech reference signal). FIG. 6 is a graph illustrating the effect of the bias parameter $\alpha$ for a range of values. In addition, FIG. 7 is a graph illustrating the effect of a maximum attenuation parameter $\gamma$ on a generated gain mask. In the example of FIG. 7, the post-filter has a bias parameter $\alpha$ equal to 0 dB (i.e., ($\alpha$=0 dB) with varying maximum attenuation parameter values (i.e., different values for $\gamma$), as shown.

As noted above, FIG. 2 generally illustrates an arrangement in which the SNR adjustment is performed prior to the post-filtering process (i.e., prior to generation of the gain mask at the parametric post-filter 264). That is, in the illustrative arrangement of FIG. 2, an additional operation is inserted after the instantaneous SNR estimation, but before the parametric post-filter 264 (e.g., before application of the parameter wiener filter) so that the instantaneous SNR estimate is adjusted in manner that normalizes the SNR separately in each frequency band, taking into account the differences in the sensor responses during detection of body noise and external acoustic sounds (i.e., differences during detection of body noise and acoustic inputs). This results in approximately the same amount of (adjustable) body noise reduction across frequencies and thus helps to avoid distortions and, in particular, reduces own voice distortions (i.e., the shape of the power spectrum of any residual/remaining body noise is substantially maintained).

Figure 8:
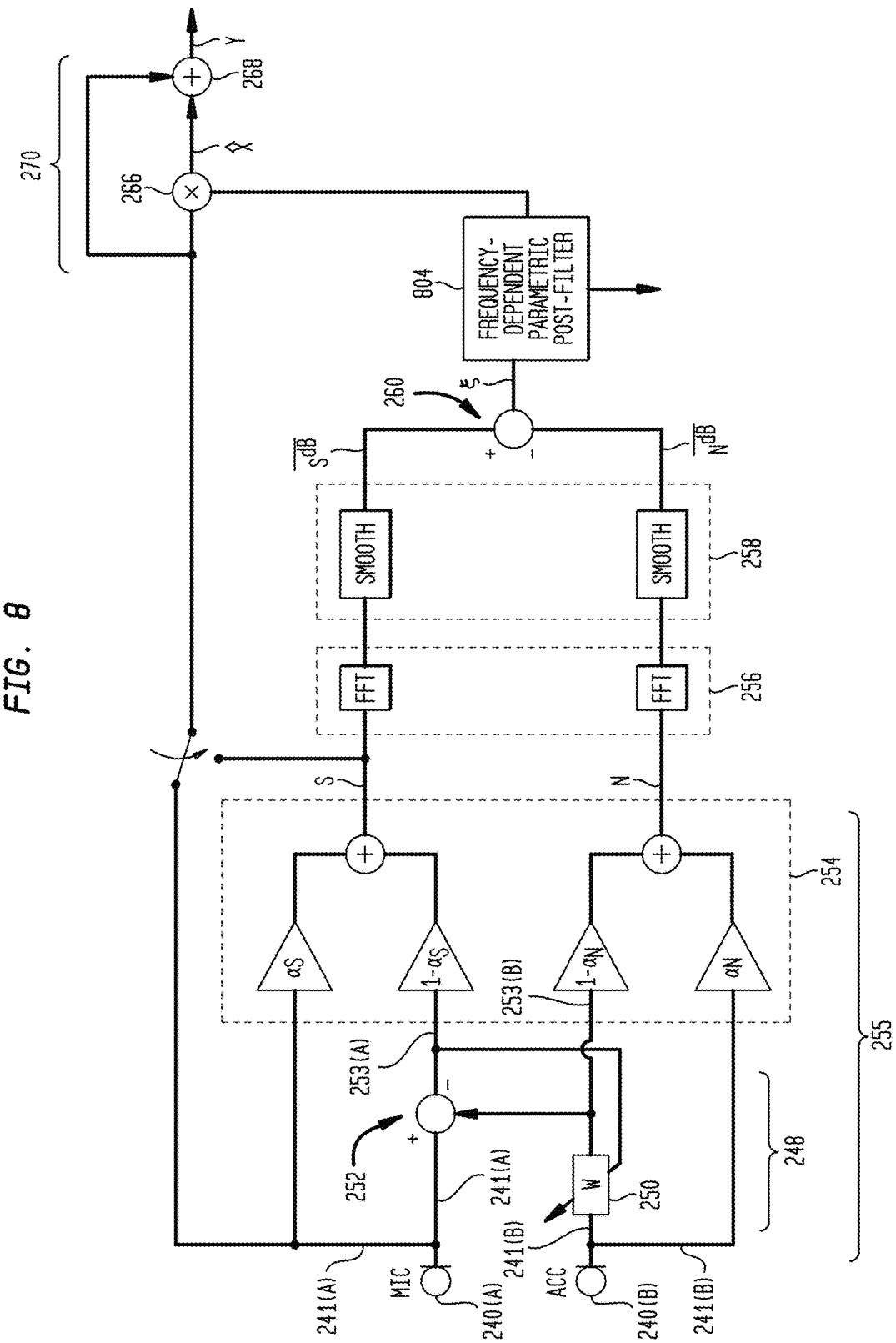
FIG. 8 is a schematic block diagram illustrating operations of a signal processor, in accordance with certain embodiments presented herein.

FIG. 8 is a schematic block diagram illustrating operations of a signal processor in accordance with certain embodiments presented herein in which a gain adjustment is performed within the post-filter that is designed to replicate or mimic the separate SNR adjustment described above. That is, FIG. 8 illustrates an arrangement in which the post-filter is configured to replicate, directly in the gain mask generation/computation, the effect of the SNR adjustment step. In these examples, the parameters of the post-filter are frequency dependent.

Shown in the illustrative embodiment of FIG. 8 is a microphone 240(A) and an accelerometer 240(B) that are configured to detect signals and operate as described above with reference to FIG. 2. FIG. 8 also illustrates the adaptive filtering stage 248, which comprises the adaptive filter 250 and the noise canceller 252, the regulation block/stage 254, the frequency domain conversion block 256, the smoothing block 258, and the SNR estimator 260, all of which may be implemented as described above with reference to FIG. 2.

In the arrangement of FIG. 8, the SNR adjustment block 262 and the parametric post-filter 264 of FIG. 2 are replaced by a frequency-dependent parametric post filter 864. In one specific example, the frequency-dependent post filter 864 is a frequency-dependent parametric wiener filter.

In the example of FIG. 8, the smoothed speech reference signal ($\overline{S^{dB}}_k[n]$), as given above in Equation 1, and the smoothed noise reference signal ($\overline{N^{dB}}_k[n]$), as given in Equation 2, are used at the SNR estimator 260 to estimate the instantaneous SNR ($\xi_k[n]$) at each frequency, as given above in Equation 3.

The instantaneous SNR ($\xi_k[n]$) is provided to the frequency-dependent parametric wiener filter 864 which, as noted above, incorporates a gain adjustment that replicates the effect of a separate SNR adjustment/normalization. More particularly, the effect of the SNR adjustment step can be replicated directly in the gain mask computation of the SNR and frequency-dependent wiener filter 864 by tuning the bias parameter ($\alpha$) and the exponent parameter ($\beta$) for each specific frequency band k (i.e., making the parameters of the post-filter variable based on the frequency processed at a given time). The operations of the frequency-dependent wiener filter 864 are represented by Equation 9, below.

$$H_k[n] = \left(\frac{\xi_k[n]}{\alpha_k + \xi_k[n]}\right)^{\beta_k} \quad \text{Equation 9}$$

In Equation 9, the bias parameter ($\alpha$) and the exponent parameter ($\beta$) are represented as $\alpha_k$ and $\beta_k$, respectively, to indicate that these parameters vary with the frequency k. The output of the SNR and frequency-dependent wiener filter 864 is a gain mask (i.e., gains at each of the k frequencies). As shown in FIG. 8, a clean signal $\hat{X}_k[n]$ is generated by applying the filter gain mask $H_k[n]$ to a signal $S_k[n]$. In the example of FIG. 8, the filter gain mask $H_k[n]$ is applied at the gain mask application module 266, as given in Equation 7 (above). As noted, $S_k[n]$ can either be the microphone signal or the speech reference signal.

Similar to FIG. 2, in certain instances the output signals $Y_k[n]$ are formed at output block 268 from a weighted combination of the signal $S_k[n]$ (e.g., either the microphone signal or the speech reference signal) and the estimated clean signal $\hat{X}_k[n]$ using a maximum attenuation parameter $\gamma$ to mix the two together. The maximum attenuation parameter $\gamma$ allows the output signals to completely disable ($\gamma=0$) or completely enable ($\gamma=1$) the noise reduction processing, with a continuous and smooth transition between the two. This is given above in Equation 8.

The result of the embodiments in both FIGS. 2 and 8 are similar in that the SNR is adjusted in a manner that normalizes the SNR separately in frequency band taking into account the differences in the sensor responses during detection of body noise only and external acoustic sound only (i.e., equalize the SNR according to the differences in the sensor responses in order to compensate for those differences). While the post-filtering in FIG. 2 utilizes a changing/variable instantaneous SNR and constant filter parameters (e.g., a constant bias parameter ($\alpha$) and a constant exponent parameter ($\beta$)), the post-filtering in FIG. 8 utilizes a constant instantaneous SNR and changing filter parameters (e.g., a frequency-dependent bias parameter ($\alpha$) and a frequency-dependent exponent parameter ($\beta$)). However, the results are similar in that application of the gain mask can produce the same amount of (adjustable) body noise attenuation across frequencies and thus helps to avoid distortions and, in particular, own voice distortions (i.e., the shape of the power spectrum of any residual/remaining body noise is substantially maintained).

The above embodiments have primarily described with reference to use of parametric wiener filters in the post-filtering process. It is to be appreciated that the use of parametric wiener filters is illustrative and that certain embodiments presented herein can include any of a number of other types of parametric post-filters that use SNR of the input sounds for generation of a gain adjustment.

FIG. 9 is a flowchart of a signal processing method 900 in accordance with certain embodiments presented herein. The signal processing method 900 begins at 902 where signals (input signals) are detected at two or more implantable sensors, and the signals comprise external acoustic sounds and body noises. At 904, a signal processor generates a speech reference signal and a noise reference signal from the signals detected at the two or more implantable sensors. At 906, the signal processor generates, with a parametric post-filter, a gain mask based on the speech reference signal and the noise reference signal. At 908, the signal processor generates output signals based on the signals detected at the two or more implantable sensors and the gain mask, wherein the output signals have a substantially reduced amount of body noise and where the amount of noise reduction is similar across frequencies thereof.

It is to be appreciated that the embodiments presented herein are not mutually exclusive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A signal processing method, comprising:
   detecting signals at two or more implantable sensors, wherein the signals detected at each of the two or more implantable sensors comprise one or more of external acoustic sounds and body noises;
   generating, from the signals detected at the two or more implantable sensors, a speech reference signal and a noise reference signal;
   determining, from the speech reference signal and the noise reference signal, instantaneous signal-to-noise ratios for the signals at a plurality of frequencies;
   adjusting the instantaneous signal-to-noise ratios at the plurality of frequencies to account for predetermined differences in responses of the two or more implantable sensors to the external acoustic sounds or the body noises;

converting, with a parametric post-filter, the instantaneous signal-to-noise ratios for the signals at a plurality of frequencies into gain values at the plurality of frequencies, wherein the gain values at the plurality of frequencies comprise a gain mask;

generating output signals based on the signals detected at the two or more implantable sensors and the gain mask, wherein the output signals have a substantially reduced amount of body noise and where the shape of the power spectrum of any residual body noise is substantially maintained.

2. The method of claim 1, wherein during conversion of the instantaneous signal-to-noise ratios at the plurality of frequencies into the gain values the plurality of frequencies, the method comprises:

adjusting one or more parameters of the parametric post-filter in correlation with the frequency of the instantaneous signal-to-noise ratios at a plurality of frequencies so as to account for predetermined differences in responses of the two or more implantable sensors to the external acoustic sounds or the body noises.

3. The method of claim 1, wherein at least one of the two or more implantable sensors comprises a microphone configured to generate an unprocessed microphone signal, and wherein generating the output signals from the signals and the gain mask comprises:

applying the gain mask to the unprocessed microphone signal.

4. The method of claim 1, wherein the parametric post-filter is a parametric wiener filter.

5. The method of claim 1, wherein the two or more implantable sensors comprise first and second sensors that are configured to generate first and second input signals, respectively, and wherein generating the speech reference signal and the noise reference signal comprises:

generating, with an adaptive filtering block, a speech estimate and a noise estimate of the signals; and controllably mixing the speech estimate with the first input signals generated by the first sensor to generate the speech reference signal; and controllably mixing the noise estimate with the second input signals generated by the second sensor to generate the noise reference signal.

6. An auditory prosthesis, comprising:

at least first and second implantable sensors configured to detect signals, wherein the second sensor is configured to be more sensitive to body noises than it is to external acoustic sound signals; and a signal processor configured to generate output signals from the signals, wherein the signal processor comprises:

an input stage configured to generate a speech reference signal and a noise reference signal from the signals, a parametric post-filter configured to generate a gain mask based on the speech reference signal and the noise reference signal, and an output stage configured utilize the gain mask to generate the output signals, wherein the gain mask is configured to normalize a signal-to-noise ratio in each of a plurality of frequency channels in the output signals to account for differences in responses of the first and second implantable sensors during detection of body noise only and external acoustic sound only.

7. The auditory prosthesis of claim 6, wherein the signal processor further comprises:

a signal-to-noise ratio estimator configured to determine, from the speech reference signal and the noise reference signal, instantaneous signal-to-noise ratios for the signals at a plurality of frequencies, wherein the parametric post-filter is configured to convert the instantaneous signal-to-noise ratios for the signals at a plurality of frequencies into gain values at the plurality of frequencies, wherein the gain values at the plurality of frequencies comprise the gain mask.

8. The auditory prosthesis of claim 7, wherein the signal processor further comprises:

a signal-to-noise ratio adjustment block configured to, prior to the parametric post-filter, adjust the instantaneous signal-to-noise ratios at the plurality of frequencies to account for predetermined differences in responses of the first and second sensors to the external acoustic sounds or the body noises.

9. The auditory prosthesis of claim 7, wherein during conversion of the instantaneous signal-to-noise ratios at the plurality of frequencies into the gain values the plurality of frequencies, the parametric post-filter is configured to adjust one or more parameters of the parametric post-filter in correlation with the frequency of the instantaneous signal-to-noise ratios at a plurality of frequencies so as to account for predetermined differences in responses of the two or more implantable sensors to the external acoustic sounds or the body noises.

10. The auditory prosthesis of claim 6, wherein the first sensor comprises an implantable microphone configured to generate an unprocessed microphone signal, and wherein the output stage is configured to apply the gain mask to the unprocessed microphone signal to generate the output signals.

11. The auditory prosthesis of claim 6, wherein the output stage is configured to apply the gain mask to the speech reference signal to generate the output signals.

12. The auditory prosthesis of claim 6, wherein the parametric post-filter is a parametric wiener filter.

13. The auditory prosthesis of claim 6, wherein the first and second sensors are configured to generate first and second input signals, respectively, and wherein the input stage comprises:

an adaptive filtering block configured to generate a speech estimate and a noise estimate of the signals based on the first and second input signals; and a regulation block configured to controllably mix the speech estimate with the first input signals generated by the first sensor to generate the speech reference signal, and to controllably mix the noise estimate with the second input signals generated by the second sensor to generate the noise reference signal.

14. The auditory prosthesis of claim 6, further comprising:

an implantable stimulator unit configured to generate, based on the outputs signals, stimulation signals for delivery to a recipient of the auditory prosthesis to evoke perception by the recipient of the signals.

15. The auditory prosthesis of claim 6, wherein the first sensor is a microphone and the second sensor is an accelerometer.

16. An auditory prosthesis, comprising:

a multi-channel implantable sensor system configured to detect input signals;

a signal processor comprising:
  an adaptive filtering block,
  a parametric post-filter operable with the adaptive filtering block in the frequency domain, wherein the parametric post-filter is configured to generate a gain mask that is tuned based on separate responses of the multi-channel implantable sensor system to external acoustic sounds and body noises,
  an output stage configured to generate, based on the input signals and the gain mask, output signals having an independently controlled amount of body noise reduction in each of a plurality of frequency bands of the output signals; and
an implantable stimulator unit configured to generate, based on the outputs signals, stimulation signals for delivery to a recipient of the auditory prosthesis to evoke perception by the recipient of the signals.

17. The auditory prosthesis of claim 16, wherein the adaptive filtering block is part of an input stage configured to generate a speech reference signal and a noise reference signal from the input signals, and wherein the parametric post-filter configured is to generate the gain mask based on the speech reference signal and the noise reference signal.

18. The auditory prosthesis of claim 17, wherein the signal processor further comprises:
  a signal-to-noise ratio estimator disposed between the input stage and the parametric post-filter, wherein the signal-to-noise ratio estimator is configured to determine, from the speech reference signal and the noise reference signal, instantaneous signal-to-noise ratios for the signals at a plurality of frequencies,
  wherein the parametric post-filter is configured to convert the instantaneous signal-to-noise ratios for the signals at a plurality of frequencies into gain values at the plurality of frequencies, wherein the gain values at the plurality of frequencies comprise the gain mask.

19. The auditory prosthesis of claim 18, wherein the signal processor further comprises:
  a signal-to-noise ratio adjustment block disposed between the signal-to-noise ratio estimator and the parametric post-filter, wherein the signal-to-noise ratio adjustment block is configured to, prior to the parametric post-filter, adjust the instantaneous signal-to-noise ratios at the plurality of frequencies to account for predetermined differences in responses of the multi-channel implantable sensor system to external acoustic sounds or body noises.

20. The auditory prosthesis of claim 18, wherein during conversion of the instantaneous signal-to-noise ratios at the plurality of frequencies into the gain values the plurality of frequencies, the parametric post-filter is configured to adjust one or more parameters of the parametric post-filter in correlation with the frequency of the instantaneous signal-to-noise ratios at a plurality of frequencies so as to account for predetermined differences in responses of the multi-channel implantable sensor system to external acoustic sounds or body noises.

21. The auditory prosthesis of claim 16, wherein the independently controlled amount of body noise reduction in each of a plurality of frequency bands of the output signals equalizes body noise reduction across the plurality of frequency bands in the output signals.

22. The auditory prosthesis of claim 16, wherein the multi-channel implantable sensor system comprises an implantable microphone configured to generate an unprocessed microphone signal, and wherein the output stage is configured to apply the gain mask to the unprocessed microphone signal to generate the output signals.

23. The auditory prosthesis of claim 17, wherein the output stage is configured to apply the gain mask to the speech reference signal to generate the output signals.

24. The auditory prosthesis of claim 17, wherein the multi-channel implantable sensor system is configured to generate first and second input signals and wherein the adaptive filtering block configured to generate a speech estimate and a noise estimate of the signals based on the first and second output signals, and wherein the input stage further comprises:
  a regulation block configured to controllably mix the speech estimate with the first output signals to generate the speech reference signal, and to controllably mix the noise estimate with the second output signals to generate the noise reference signal.

25. The auditory prosthesis of claim 16, wherein the parametric post-filter is a parametric wiener filter.

26. The auditory prosthesis of claim 16, wherein the multi-channel implantable sensor system comprises at least first and second implantable sensors configured to detect the signals, wherein the second sensor is configured to be more sensitive to body noises than it is to external acoustic sound signals.

27. The auditory prosthesis of claim 16, wherein the first sensor is a microphone and the second sensor is an accelerometer.

* * * * *

UNITED STATES PATENT AND TRADEMARK OFFICE
CERTIFICATE OF CORRECTION

PATENT NO. : 10,463,476 B2  
APPLICATION NO. : 15/581200  
DATED : November 5, 2019  
INVENTOR(S) : Federico Bolner et al.

Page 1 of 1

It is certified that error appears in the above-identified patent and that said Letters Patent is hereby corrected as shown below:

In the Claims

In Column 15, Line 8, Claim 1 after "mask;" insert --and--

In Column 15, Line 12, Claim 1 after "where" change "the" to --a--

In Column 15, Line 12, Claim 1 after "of" change "the" to --a--

In Column 16, Line 27 and 28, Claim 9 change "two or more" to --first and second--

In Column 18, Line 29, Claim 24 delete "first"

In Column 18, Line 30, Claim 24 delete "and second"

In Column 18, Line 33, Claim 24 change "the first" to --at least a first one of the--

In Column 18, Line 35, Claim 24 change "the second" to --at least a second one of the--

In Column 18, Line 45, Claim 27 after "first" insert --implantable--

In Column 18, Line 46, Claim 27 after "second" insert --implantable--

Signed and Sealed this  
Tenth Day of December, 2019

Andrei Iancu  
*Director of the United States Patent and Trademark Office*